(12) United States Patent
Ferree et al.

(10) Patent No.: US 7,235,102 B2
(45) Date of Patent: Jun. 26, 2007

(54) PROSTHETIC COMPONENTS WITH CONTAINED COMPRESSIBLE RESILIENT MEMBERS

(76) Inventors: Bret A. Ferree, 1238 Cliff Laine Dr., Cincinnati, OH (US) 45208; Timothy L. Ferree, 3803 W. St. Rt. 185, Piqua, OH (US) 45356

( * ) Notice: Subject to any disclaimer, the term of this patent is extended or adjusted under 35 U.S.C. 154(b) by 194 days.

(21) Appl. No.: 10/434,917

(22) Filed: May 9, 2003

(65) Prior Publication Data
US 2004/0044410 A1 Mar. 4, 2004

Related U.S. Application Data

(60) Provisional application No. 60/379,462, filed on May 10, 2002.

(51) Int. Cl.
*A61F 2/44* (2006.01)
(52) U.S. Cl. .................................................. 623/17.12
(58) Field of Classification Search ... 623/17.11–17.16
See application file for complete search history.

(56) References Cited

U.S. PATENT DOCUMENTS

| | | | | |
|---|---|---|---|---|
| 4,309,777 A | * | 1/1982 | Patil | 623/17.13 |
| 4,759,769 A | | 7/1988 | Hedman et al. | 623/17.13 |
| 4,863,477 A | * | 9/1989 | Monson | 623/17.12 |
| 4,932,975 A | * | 6/1990 | Main et al. | 623/17.12 |
| 5,002,576 A | | 3/1991 | Fuhrmann et al. | 623/17.15 |
| 5,047,055 A | * | 9/1991 | Bao et al. | 623/17.16 |
| 5,071,437 A | * | 12/1991 | Steffee | 623/17.16 |
| 5,389,107 A | | 2/1995 | Nassar et al. | 623/23 |
| 5,458,642 A | | 10/1995 | Beer et al. | 623/17.13 |
| 5,676,702 A | | 10/1997 | Ratron | 623/17.16 |
| 5,865,846 A | | 2/1999 | Bryan et al. | 128/898 |
| 5,989,291 A | | 11/1999 | Ralph et al. | 623/17.15 |
| 6,001,130 A | | 12/1999 | Bryan et al. | 623/17.16 |
| 6,022,376 A | | 2/2000 | Assell et al. | 623/17.16 |
| 6,063,121 A | | 5/2000 | Xavier et al. | 623/17.15 |
| 6,136,031 A | | 10/2000 | Middleton | 623/17.16 |
| 6,156,067 A | | 12/2000 | Bryan et al. | 623/17.15 |
| 6,231,609 B1 | * | 5/2001 | Mehdizadeh | 623/17.11 |
| 6,258,126 B1 | * | 7/2001 | Colleran | 623/20.29 |
| 6,296,664 B1 | | 10/2001 | Middleton | 623/17.15 |
| 6,315,797 B1 | | 11/2001 | Middleton | 623/17.16 |
| 6,402,785 B1 | * | 6/2002 | Zdeblick et al. | 623/17.16 |

(Continued)

FOREIGN PATENT DOCUMENTS

WO  WO 00/59412  10/2000

(Continued)

*Primary Examiner*—Suzette Gherbi
(74) *Attorney, Agent, or Firm*—Gifford, Krass, Sprinkle, Anderson & Citkowski, PC

(57) ABSTRACT

One or more rigid components associated with an articulating bone are used to encase, encapsulate, contain, or otherwise protect a compressible/resilient member. The embodiments are applicable not only to artificial disc replacement (ADR) devices, but also to joint situations including total knee and hip arthroplasty. The cushion elements in the preferred embodiments include synthetic rubbers, hydrogels, elastomers, and other polymeric materials such as viscoelastic polymers and foam polyurethanes. The invention effectively combines the advantages of such materials (cushioning, shape memory, and expansion after insertion in the case of hydrogels), while providing increased protection, particularly the elimination of shear stresses. When applied to an ADR, the invention also minimizes the risk of extrusion.

2 Claims, 9 Drawing Sheets

U.S. PATENT DOCUMENTS

| | | | |
|---|---|---|---|
| 6,508,841 B2 | 1/2003 | Martin et al. | 623/23.12 |
| 6,520,996 B1 | 2/2003 | Manasas et al. | 623/23.5 |
| 6,527,806 B2 | 3/2003 | Ralph et al. | 623/17.16 |
| 6,533,818 B1 * | 3/2003 | Weber et al. | 623/17.16 |
| 7,094,257 B2 * | 8/2006 | Mujwid et al. | 623/17.15 |
| 2004/0225361 A1 * | 11/2004 | Glenn et al. | 623/17.12 |
| 2005/0015152 A1 * | 1/2005 | Sweeney | 623/17.14 |
| 2005/0033437 A1 * | 2/2005 | Bao et al. | 623/17.15 |

FOREIGN PATENT DOCUMENTS

| | | |
|---|---|---|
| WO | WO 00/64385 | 11/2000 |

* cited by examiner

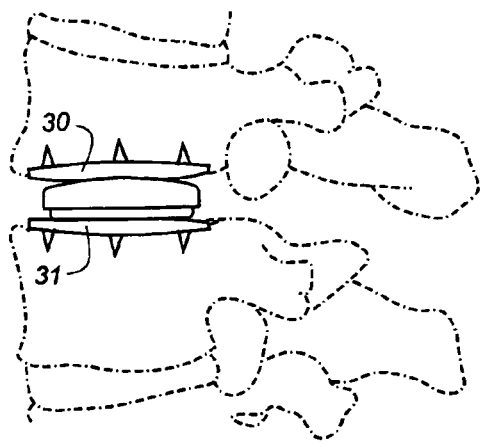
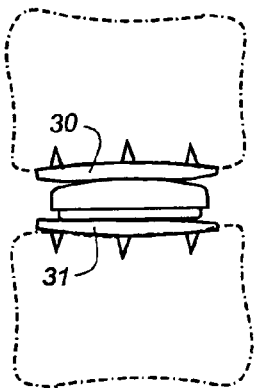
*Fig - 6A*
*Fig - 6B*
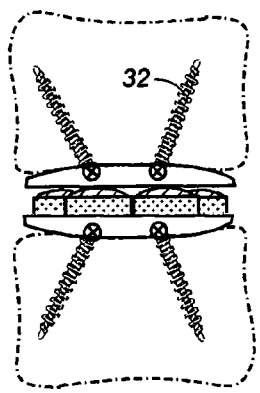
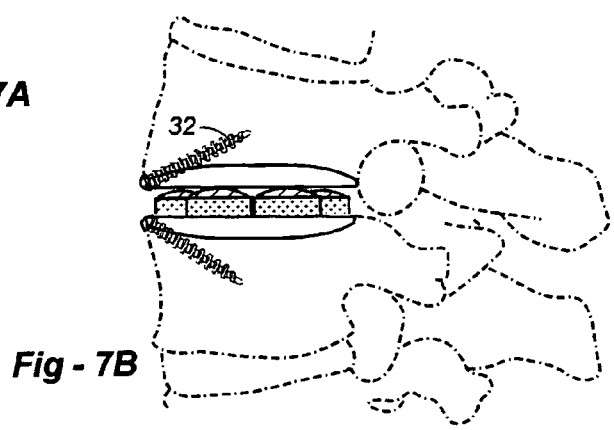
*Fig - 7A*
*Fig - 7B*
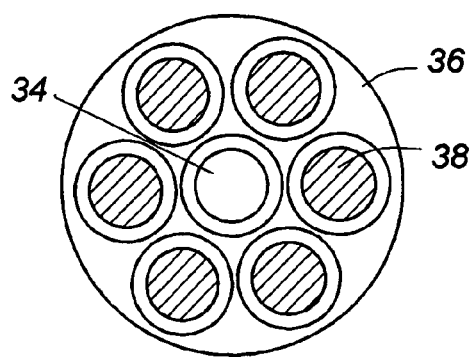
*Fig - 7C*
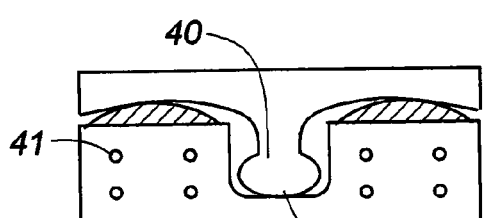
-OR-
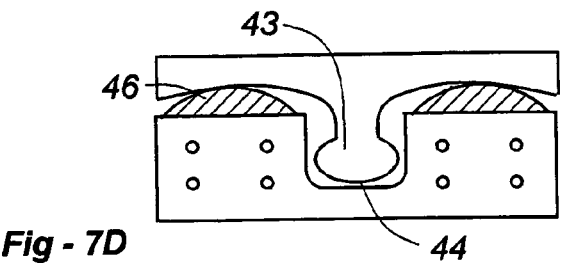
*Fig - 7D*

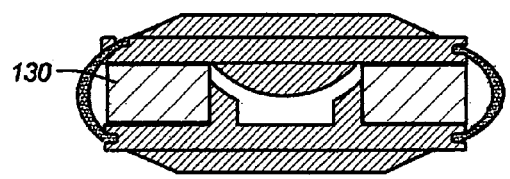
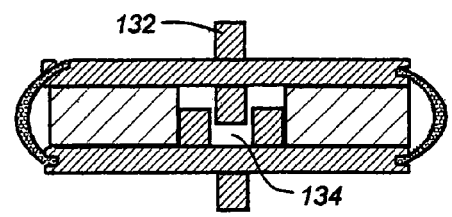
Fig - 24A     Fig - 24B
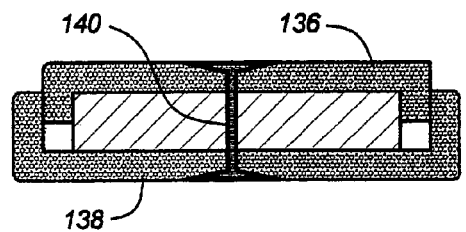
Fig - 26
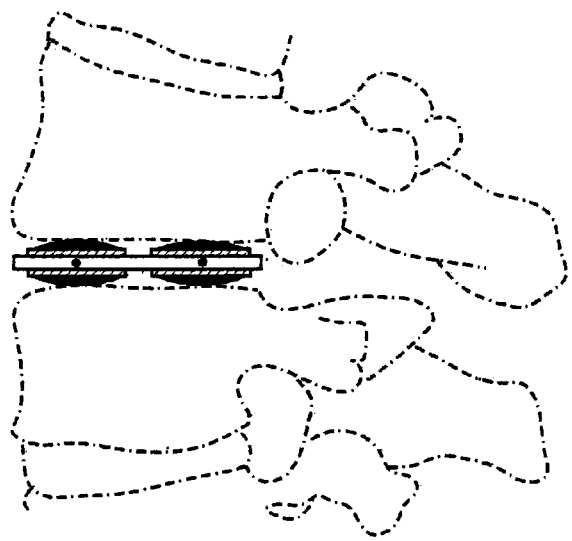
Fig - 25

PROSTHETIC COMPONENTS WITH CONTAINED COMPRESSIBLE RESILIENT MEMBERS

REFERENCE TO RELATED APPLICATION

This application claims priority from U.S. Provisional Patent Application Ser. No. 60/379,462, filed May 10, 2002, the entire content of which is incorporated herein by reference.

FIELD OF THE INVENTION

This invention relates generally to prosthetic implants and, more particularly, to devices of this type including contained, compressible, resilient members.

BACKGROUND OF THE INVENTION

Artificial disc replacements (ADRs) are frequently made of hydrogels or metal and rubber. Hydrogel ADRs generally surround the hydrogel core with a flexible constraining jacket, as shown in PCT/USOO/80920, WO 00/59412.

Unfortunately, the flexibility of the hydrogel and the constraining jacket allow hydrogel ADRs to change shape and extrude through defects in the annulus through which the ADR was inserted, for example. Metal and rubber ADRs often fail at the metal-rubber interface. The rubber fails with the high shear stresses or the rubber separates from the metal with shear stress.

There does exist issued patents that relate to enclosing or sealing hydrogel materials. Of interest is U.S. Pat. No. 6,022,376, which teaches a hydrogel enclosed by a fluid permeable bag. However, the fluid bag does little to protect the hydrogel from shear stress, and the rough texture of the bag may cause hydrogel wear from friction.

U.S. Pat. No. 5,002,576 teaches an elastomer enclosed by rigid cover plates and a corrugated tube. The elastomer is sealed from fluids of the body. The corrugated tube allows movement of the cover plates. The corrugated tube may reduce shear forces on the elastomer. U.S. Pat. Nos. 5,865, 846; 6,001,130; and 6,156,067 teach a spherical articulation between ADR EPs and an elastomer. The elastomer may be sealed within the ADR EPs. An annular gasket may reduce shear forces on the elastomer. U.S. Pat. No. 5,893,889 teaches an elastomer that is sealed between ADR EPs. The device uses a ball and socket feature to reduce shear on the elastomer. U.S. Pat. No. 6,063,121 incorporates X-shaped wires into the '889 device to reduce rotation.

SUMMARY OF THE INVENTION

In broad and general terms, this invention encases, encapsulates, contains, or otherwise protects a compressible/resilient member with one or more rigid components associated with an articulating bone. The embodiments are applicable not only to artificial disc replacement (ADR) devices, but also to joint situations including total knee and hip arthroplasty. The cushion elements in the preferred embodiments include synthetic rubbers, hydrogels, elastomers, and other polymeric materials such as viscoelastic polymers and foam polyurethanes. The invention effectively combines the advantages of such materials (cushioning, shape memory, and expansion after insertion in the case of hydrogels), while providing increased protection, particularly the elimination of shear stresses. When applied to an ADR, the invention also minimizes the risk of extrusion.

The container that surrounds the cushion element may perform multiple advantageous functions, including:
  A. Holds the cushion in place.
  B. Reduces frictional forces on the cushion element.
  C. Reduces shear forces on the cushion element.
  D. In some embodiments, seals the cushion element from exposure to the fluids of the body. Body fluids may destroy the cushion element.
  E. In some embodiments, retains particle debris.
  F. Prevents the growth of tissues into the ADR. Tissue ingrowth may limit the motion of ADRs.

One disclosed ADR-related embodiment incorporates a polymer cushion element, including elastomers and hydrogels, surrounded by a rigid component or rigid components, to accommodate repeated compression of the cushion element by movement of the rigid component or between the rigid components. This system is may be achieved with or without ADR endplates.

According to a different preferred embodiment, an ADR encloses a polymer cushion element, including elastomers and hydrogels, in a single somewhat flexible metal or plastic component. Alternatively, an ADR with a modular cushion element can be replaced through a removable portion of an outer surrounding component. The surrounding component itself can also be removable. Another ADR according to the invention uses thin rigid liners over elastomer to reduce the friction between the elastomer and ADR EPs. A different embodiment incorporates a novel, motion-limiting keel.

Elastomers, or other polymers, may be provided with caps to reduce friction and wear on the polymer. More than two disc spacer ADRs (ADR without endplates) may be interconnected; more than one polyurethane component may be present in an ADR, and more than two components may interact to limit axial rotation.

BRIEF DESCRIPTION OF THE DRAWINGS

FIG. 6A is a side-view of the device of FIG. 5A with inferior and superior end plates attached to the respective vertebrae;

FIG. 6B is an anterior-posterior view of the device of FIG. 6A in position;

FIG. 7A is an anterior-posterior view of in partial cross-section of an ADR incorporating multiple cylinders;

FIG. 7B is a side-view, also in partial cross-section;

FIG. 7C is an axial cross-section of a device containing a central guide cylinder surrounding six pistons;

FIG. 7D shows two embodiments with multiple cylinders;

FIG. 24A is a sagittal cross section through another embodiment of the ADR;

FIG. 24B is a coronal cross section through the ADR drawn in FIG. 24A;

FIG. 25 is a lateral view of the spine and a multi-component embodiment of the ADR drawn in FIG. 2A; and FIG. 26 is a sagittal cross section through the embodiment of the ADR drawn in FIG. 5A.

DETAILED DESCRIPTION OF THE INVENTION

This invention addresses and solves problems associated with artificial disc replacement (ADR) devices and joint-related components, including those associated with total-knee and hip arthroplasty, by effectively combining the advantages of hydrogels and other compressible/resilient materials while minimizing shear stresses. When applied to an ADR, the invention also minimizes the risk of extrusion. Hydrogels are used in the preferred embodiments. U.S. Pat. Nos. 5,047,055 and 5,192,326, both incorporated by reference, list some of the applicable hydrogels. The small size of the desiccated hydrogel facilitates insertion, after which the hydrogel imbibes fluids and expands. Other non-hydrogel compressible and/or resilient materials may alternatively be used, including elastomers, shape-memory polymers, which would increase in height after they are inserted. As another example of many, non-hydrogel polymers such as acrylics may be used which change shape with a change in temperature. Thus, as used herein, the term "hydrogel" should be taken to include other resilient/compressible materials.

According to the invention, the hydrogels are protected from shear stress, thereby extending longevity. In particular, the hydrogel is contained, constrained or enclosed within a cavity or cylinder which may include one or more pistons. The hydrogel provides cushioning, while the metal pistons facilitate articulation either directly or indirectly with bone surfaces. Thus, the invention offers the advantages of metal-on-metal while providing for cushioning. The hydrogels allow for physiologic tension adjustment since they can change size based upon imbibing fluid and the pressure on the hydrogel. Thus, the hydrogel component of the device can change height to balance the forces against the surrounding tissues.

The cylinder and piston would likely be made of metal such as stainless steel, titanium, chrome cobalt, or other biocompatible metal or ceramic alloy. Surfaces to promote bone ingrowth could be used on the covers. The hydrogel embodiments may incorporate channels for the diffusion of fluids in and out of the cylinder. Optional permeable membranes can also be used to prevent extrusion of the hydrogel through the channels. The permeable membrane traps the hydrogel but allows fluids to move freely across the membrane.

Figure 1A:
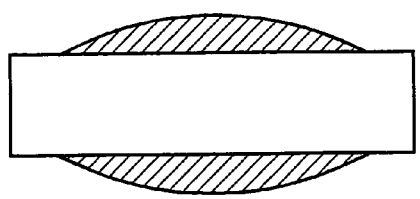
FIG. 1A is a side view of a contained artificial disc replacement (ADR) of the present invention.
Figure 1B:
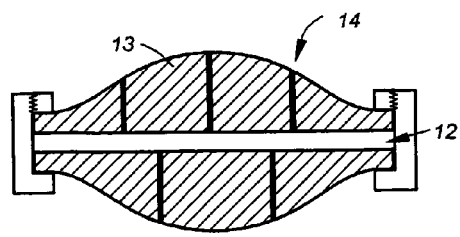
FIG. 1B shows the cross-section of the device of FIG. 1A.
Figure 1C:
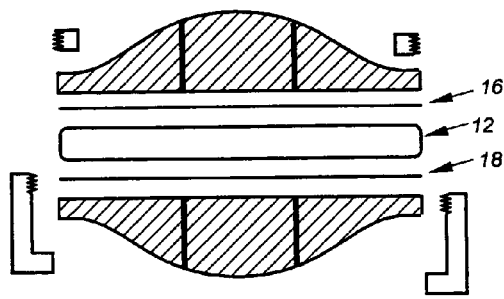
FIG. 1C is an exploded view of the device of FIGS. 1A and 1B.
Figure 1E:
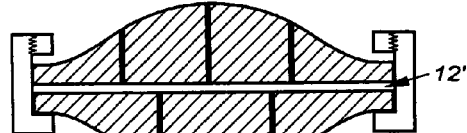
FIG. 1E shows the device in a dehydrated state.
Figure 1D:
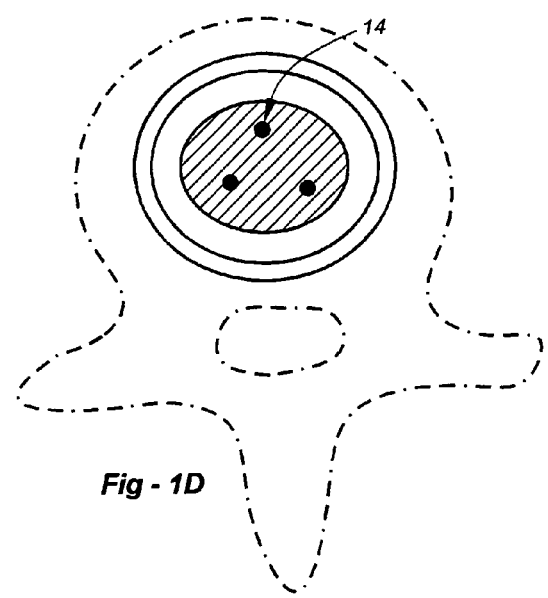
FIG. 1D is a top view of FIGS. 1A-1C in position between a pair of adjacent vertebrae.
Figure 1F:
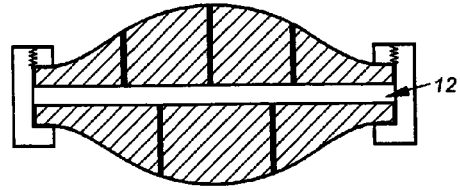
FIG. 1F shows the device in a hydrated/expanded state.

FIG. 1A is a side view of a contained artificial disc replacement (ADR) according to the invention. FIG. 1B is a drawing that shows cross-section of the device of FIG. 1A. FIG. 1C is an exploded view of the device of FIGS. 1A and 1B. FIG. 1D is a top view of FIGS. 1A-1C in position between a pair of adjacent vertebrae. FIG. 1E shows the device in a dehydrated state; FIG. 1F shows the device in a hydrated/expanded state.

Figure 2A:
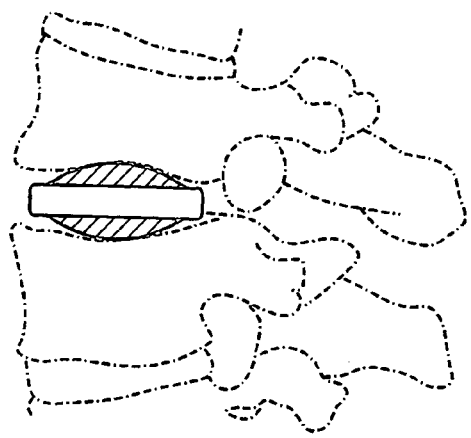
FIG. 2A shows an ADR according to the present invention disposed symmetrically between adjacent vertebrae.
Figure 2B:
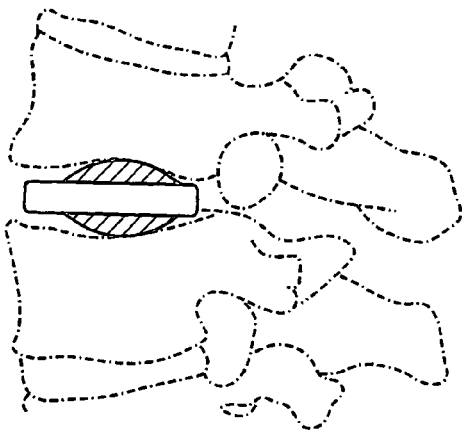
FIG. 2B illustrates an asymmetrical configuration.
Figure 3A:
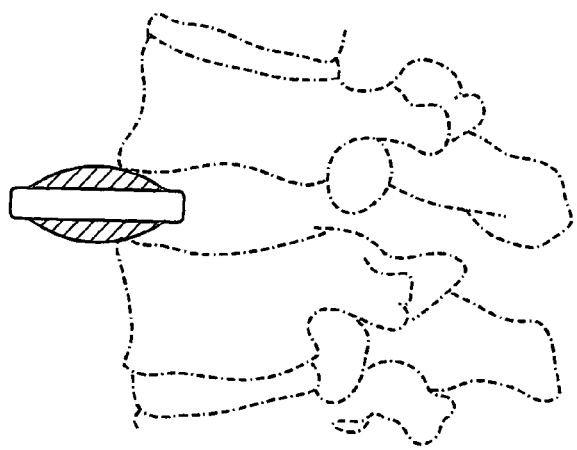
FIG. 3A illustrates a device dehydrated for insertion between the vertebrae.
Figure 3B:
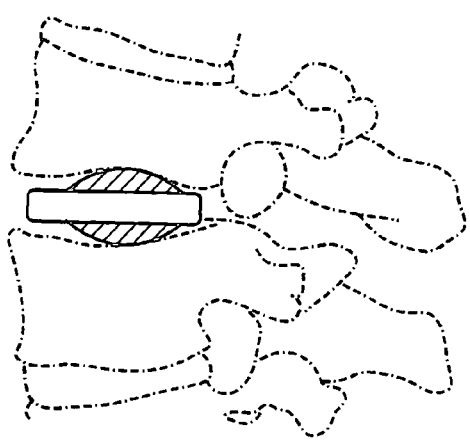
FIG. 3B illustrates the device expanded after insertion and hydration.
Figure 4A:
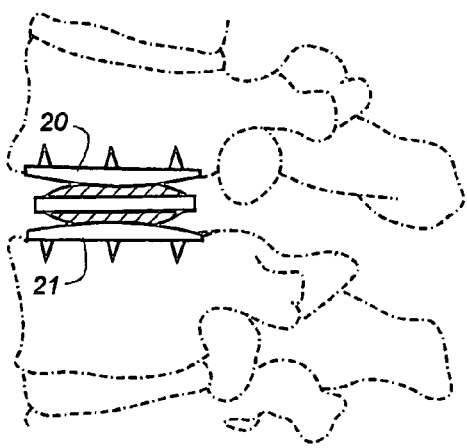
FIG. 4A shows the device of the present invention with endplates in position.
Figure 4B:
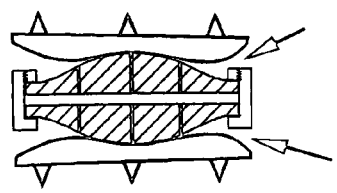
FIG. 4B is a cross-section of FIG. 4A.

Devices according to the invention, regardless of disposition in the body, may be placed symmetrically or asymmetrically. FIG. 2A shows an ADR according to the invention disposed symmetrically between adjacent vertebrae. FIG. 2B illustrates an asymmetrical configuration. FIG. 3A illustrates a device dehydrated for insertion between the vertebrae and FIG. 3B illustrates the device expanded after insertion and hydration. As shown in FIG. 4, endplate covers may be provided in conjunction with the contained hydrogel ADR according to the invention. FIG. 4A shows the device and endplates in position. FIG. 4B is a cross-section.

Figure 5A:
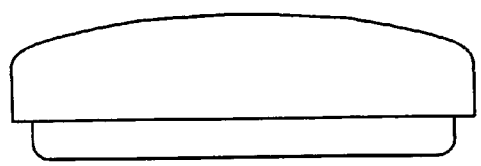
FIG. 5A is a simplified side view of an alternative embodiment of an ADR.
Figure 5B:
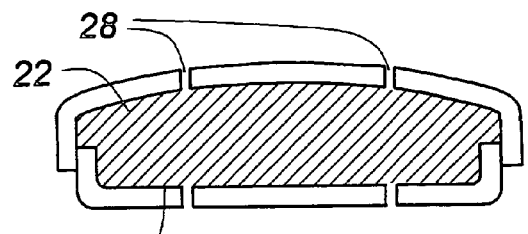
FIG. 5B shows a cross-section of the more encapsulated device showing channels for facilitate fluid transfer.
Figure 5C:
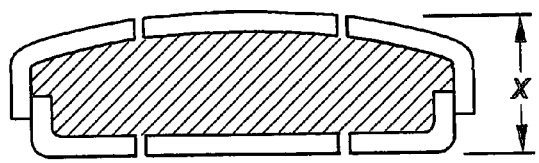
FIG. 5C is a cross-section showing the hydrogel in a desiccated state.
Figure 5D:
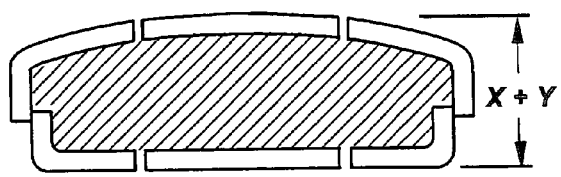
FIG. 5D is a cross-section showing the hydrogel in a hydrated, expanded form.
Figure 5E:
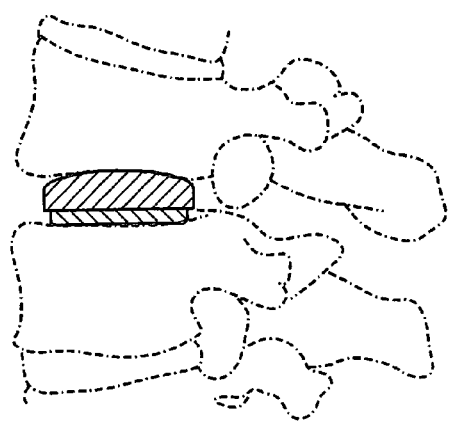
FIG. 5E shows the side view of the device in place between upper and lower vertebrae.
Figure 5F:
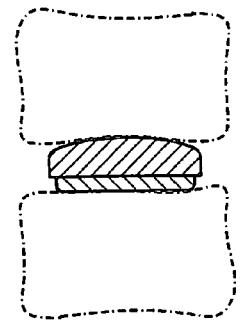
FIG. 5F is an anterior-posterior view of the device in place.

FIG. 5A is a simplified side view of an alternative ADR according to the invention, wherein the hydrogel is further encapsulated. FIG. 5B is a cross-section of the more encapsulated device showing channels for facilitate fluid transfer. FIG. 5C is a cross-section showing the hydrogel in a desiccated state. FIG. 5D is a cross-section showing the hydrogel in a hydrated, expanded form. FIG. 5E shows the device in place between upper and lower vertebrae from a side view. FIG. 5F is an A-P of the device in place. FIG. 6A is a side-view of the device of FIG. 5, with inferior and superior end plates attached to the respective vertebrae. FIG. 6B is an A-P view of the device of FIG. 6A in position.

The invention may also include two or more cylinders. Adding cylinders reduces the tendency of a single assembly to tilt when pressure is applied in an eccentric fashion. FIG. 7A is an A-P view of in partial cross-section of an ADR incorporating multiple cylinders. FIG. 7B is a side-view, also in partial cross-section. FIG. 7C is an axial cross-section of a device containing a central guide cylinder surrounding six pistons. It will be appreciated that more or fewer guide cylinders and/or pistons may be used as shown, for example, in FIG. 10.

FIG. 7D shows two embodiments with multiple cylinders. In the partial cushion embodiment (upper drawing), the spherical end of the peg projecting from the top plate rests against and is partially supported by a concavity in the lower plate. In the full cushion embodiment (lower drawing), the peg projecting from the top plate fits into a restraining cylinder. The peg form the top plate does not rest against the bottom plate in this embodiment. In either case, the end of the peg is preferably spherical to allow angular motion between the two plates.

Figure 8A:
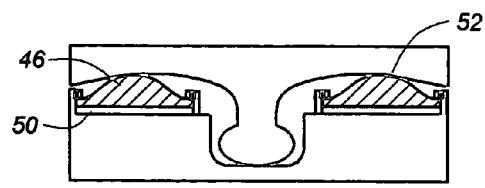
FIG. 8A is a coronal/sagittal cross-section of the cylinders according to the present invention.
Figure 8B:
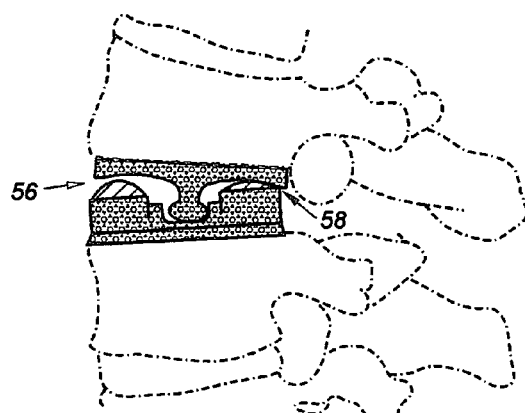
FIG. 8B is an illustration of two vertebrae in extension.
Figure 9:
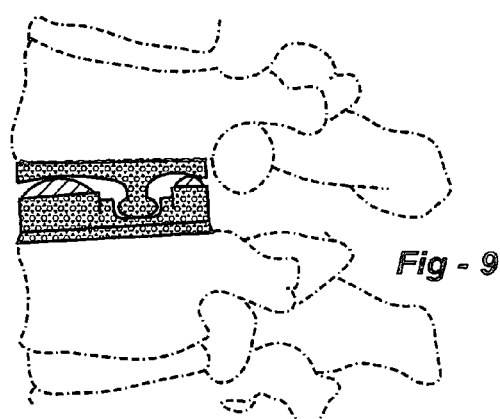
FIG. 9 shows an embodiment with the peg projecting from the posterior aspect of the inferior surface of the upper plate.

FIG. 8A is a coronal/sagittal cross-section of the cylinders according to this embodiment of the invention. FIG. 8B is an illustration of two vertebrae in extension, showing the way in which the front piston is raised and the back piston is lowered. Note that the peg that projects from the lower portion of the upper plate need not be central in location. FIG. 9 shows an embodiment with the peg projecting from the posterior aspect of the inferior surface of the upper plate. Posterior peg placement allows a larger anterior cylinder. The larger anterior cylinder may be better at handling the larger forces placed on the anterior portion of the disc replacement during spinal flexion.

Figure 10B:
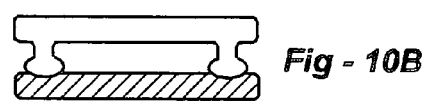
FIG. 10B is a frontal view in cross-section showing partial cushioning.
Figure 10A:
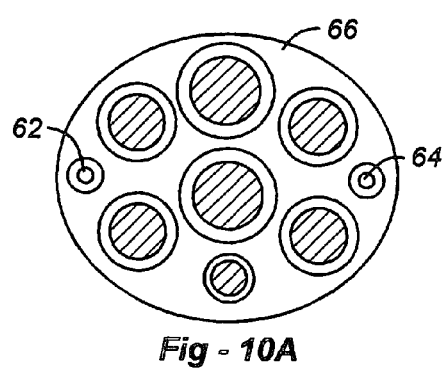
FIG. 10A shows a further alternative embodiment of the present invention.
Figure 10C:
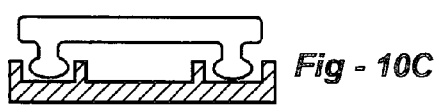
FIG. 10C is a frontal cross-sectional view illustrating full cushioning.
Figure 11B:
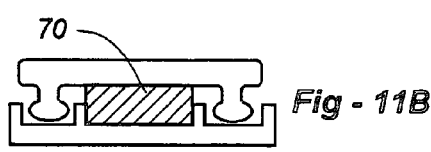
FIG. 11B is a side-view drawing in cross-section showing partial cushioning of the device of FIG. 11A.
Figure 11C:
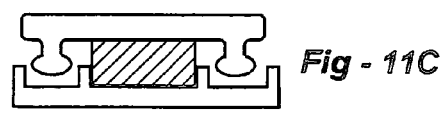
FIG. 11C is a side-view drawing in partial cross-section illustrating the embodiment of FIGS. 11A and 11B.
Figure 11A:
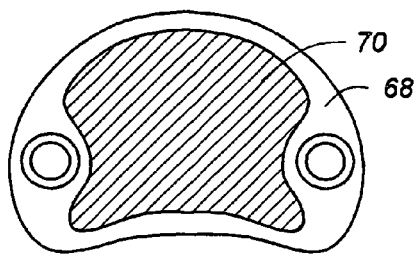
FIG. 11A is a top-down view of an embodiment showing opposing retaining cylinders on either side of a central resilient member.

FIG. 10 is a drawing which shows an alternative arrangement wherein multiple guide cylinders are used at the periphery as opposed to a central location. Among other advantages, this may help to prevent rotatory subluxation of the top component relative to the bottom component while allowing more area centrally for the hydrogels/polymer cylinders. FIG. 10A is a top cross-section view of an embodiment showing multiple peripheral cylinders and additional internal hydrogel chambers. FIG. 10B is a frontal view in cross-section showing partial cushioning. FIG. 10C is a frontal cross-sectional view illustrating full cushioning. Two or more retaining cylinders may also be used to reduce the shear on the solid piece of silicone rubber, elastomer or hydrogel-type material. FIG. 11A is a top-down view of an embodiment showing opposing retaining cylinders on either side of a central resilient member. FIG. 11B is a side-view drawing in cross-section showing partial cushioning of the device of FIG. 11A. FIG. 11C is a side-view drawing in partial cross-section illustrating the embodiment of FIGS 11A and 11B providing a full cushioning and reduced shear capability.

Figure 12A:
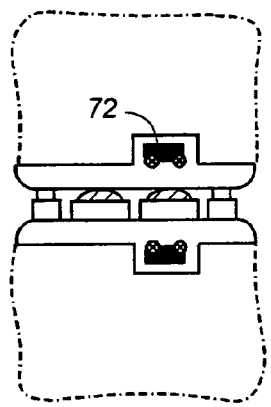
FIG. 12A shows an anterior-posterior view of the embodiment of the invention wherein the end plates of ADR may contain hollow keels on the vertebral side.
Figure 12B:
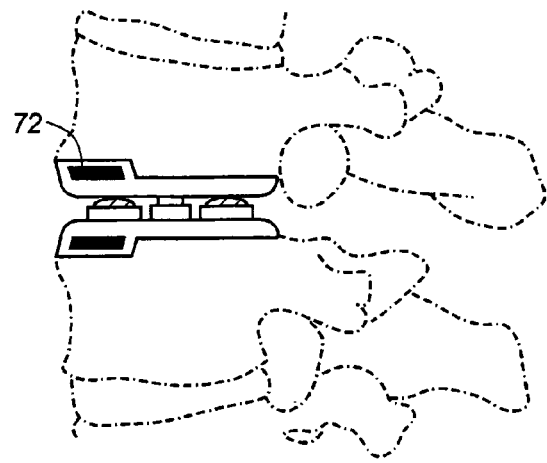
FIG. 12B is a lateral view of FIG. 12A.
Figure 12C:
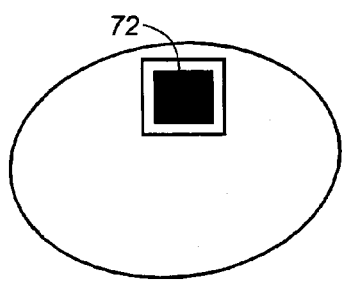
FIG. 12C is a top-down view illustrating the bone ingrowth area of FIG. 12A.

Reference is now made to FIG. 12A, which is an A-P view of the embodiment of the invention wherein the end plates of ADR may contain hollow keels on the vertebral side. FIG. 12B is a lateral view and, FIG. 12C is a top-down view illustrating the bone ingrowth area. The vertebrae would be osteotomized to make room for the keels. The bone from the osteomity sites would be morselized and placed inside the hollow keels. The morselized bone would promote ingrowth into the end plates of the ADR, much like hollow cages promote bone ingrowth.

Figure 13:
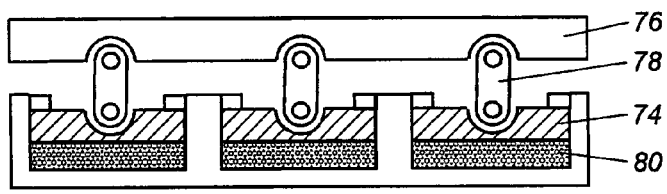
FIG. 13 is a cross-section of an embodiment with multiple pistons connected to the top plate via a rod.
Figure 14A:
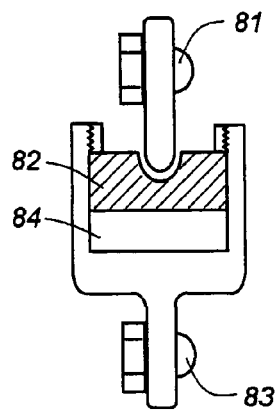
FIG. 14A is a cross-section illustrating an anterior-posterior view of two pedicle screws.
Figure 14B:
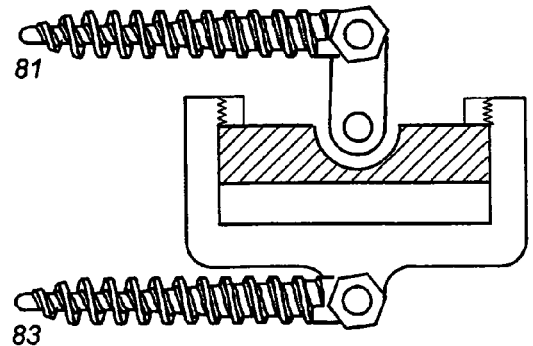
FIG. 14B is a cross-sectional lateral view of the embodiment of FIG. 14A.
Figure 15A:
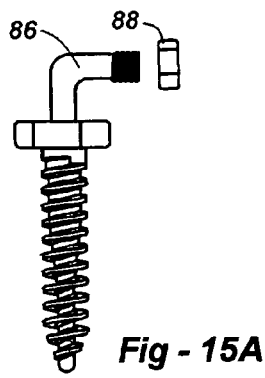
FIG. 15A is a side-view of a pedicle screw having an axle to receive a shock absorber according to the present invention.
Figure 15B:
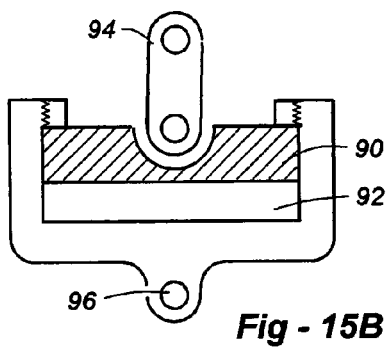
FIG. 15B is a close-up of the shock absorber mechanism associated with a pedicle screw embodiment of FIG. 15A.

FIG. 13 is a cross-section of an embodiment with multiple pistons connected to the top plate via rod, much like the design of rods that connect pistons to a crankshaft in an engine. The shock absorber concept according to this invention may also be used with respect to vertebral shock absorbers. FIG. 14A is a cross-section illustrating an A-P view of two pedicle screws coupled in this way. FIG. 14B is a cross-sectional lateral view of the embodiment of FIG. 14A. FIG. 15A is a side-view of a pedicle screw having an axle to receive a shock absorber according to the invention. FIG. 15B is a close-up of the shock absorber mechanism associated with a pedicle screw embodiment.

The cylinders could be made of ceramic, metal, or metal lined with ceramic. The pistons could also be made of metal, ceramic, alloys and so forth. In any case, the articulation of the top and bottom plates is preferably metal-to-metal or ceramic-to-metal, both of which are presumably superior to metal-to-polyethylene articulations. Furthermore, hydrogels, shape memory polymers, or other polymers within the cylinder provide a cushion, or dampen the forces across the plates.

Polymers of different durometers could be used in cylinders in different locations. For example, the polymers in the posterior cylinders could be less compressible and therefore help resist extension of the spine. The cylinders could also use liquids with baffles to dampen motion. That said, hydrogels or polymers have the benefit of functioning without a water tight cylinder piston unit. Indeed, as mentioned previously, the cylinders or the pistons may contain holes to allow fluid movement in the hydrogel configurations.

As discussed above, this invention is not limited to the spine, but may be used in other joint situations such as the knee and hip, which typically use polyethylene bearing surfaces on the acetabulum or proximal tibia. Problems related to polyethylene wear are well known to orthopedic surgeons. Although metal-on-metal and ceramic-on-ceramic total hips have been developed to reduce the problems associated with poly wear, such designs do not provide shock-absorbing capacity. For example, excessive force form tight ligaments about the knee or hip may reduce the size of the hydrogel, thus reducing the tension on the ligaments. Conversely, loose ligaments will cause the hydrogel to swell, thus increasing the tension on the loose ligaments. Although hydrogels are used in this preferred embodiment as well, other elastomers and polymers including shape memory polymers may alternatively be used.

Figure 16:
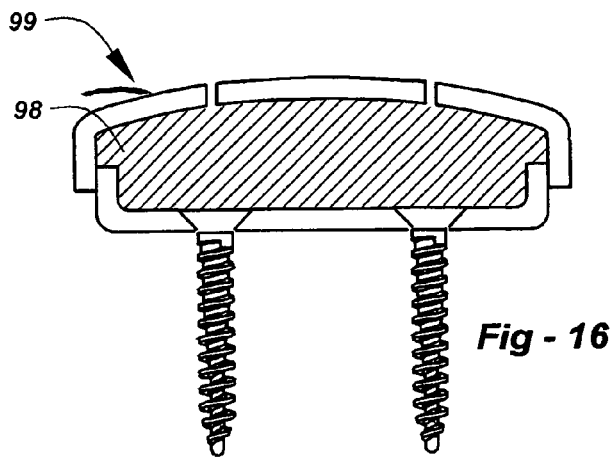
FIG. 16 is a cross-sectional view of a tibial component according to the present invention.
Figure 17:
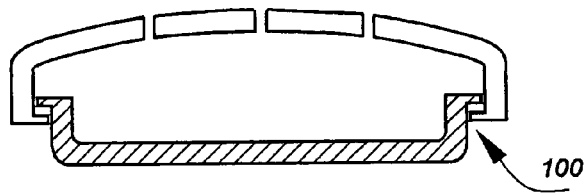
FIG. 17 is a drawing which shows how a locking component may be incorporated in the design.
Figure 18:
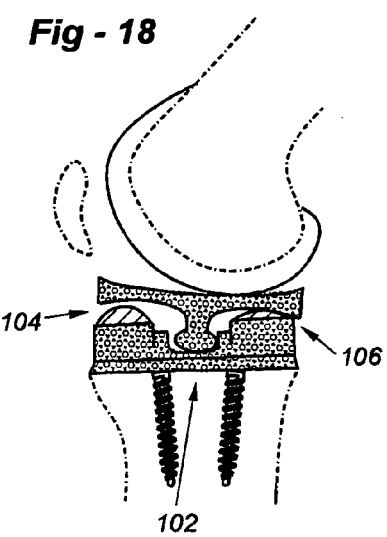
FIG. 18 is a side-view cross-section of a tibial component for a knee replacement.

FIG. 16 is a cross-sectional view of a tibial component according to the invention. As discussed above, channels are used for fluid transfer, and these may be located around the periphery, or near the center, rather than in the weight-bearing area. FIG. 17 is a drawing which shows how a locking component may be incorporated in the design which allows movement while, at the same time, prevent disassociation. A similar design may be used for other prosthetic components, including a patella button. FIG. 18 is a side-view cross-section of a tibial component for a knee replacement utilizing a central guide and peripheral pistons, much like the vertebral embodiments discussed with reference to FIGS. 7-11, in particular.

Figure 19:
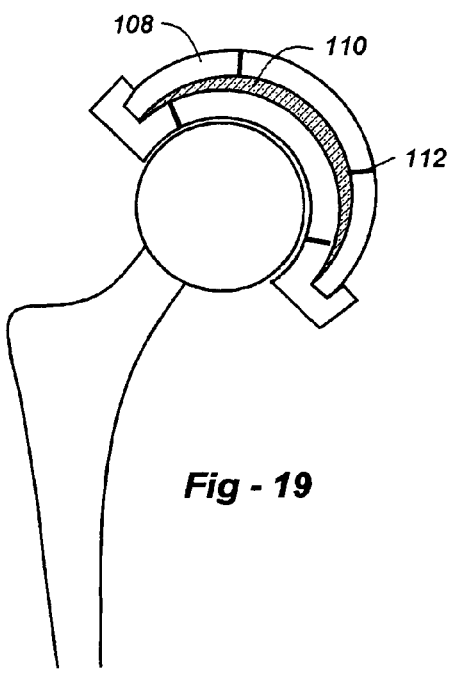
FIG. 19 is a side-view drawing of an embodiment illustrating the way in which the invention may be applied to the hip.

FIG. 19 is a side-view drawing of an embodiment illustrating the way in which the invention may be applied to the hip. As shown in the drawing, an inner cup would be used with respect to the acetabulum, along with an outer bearing surface with a hydrogel/elastomeric or other polymeric material being used therebetween. Particularly with regard to a hydrogel configuration, one or more channels for fluid transfer may be provided.

Figure 20:
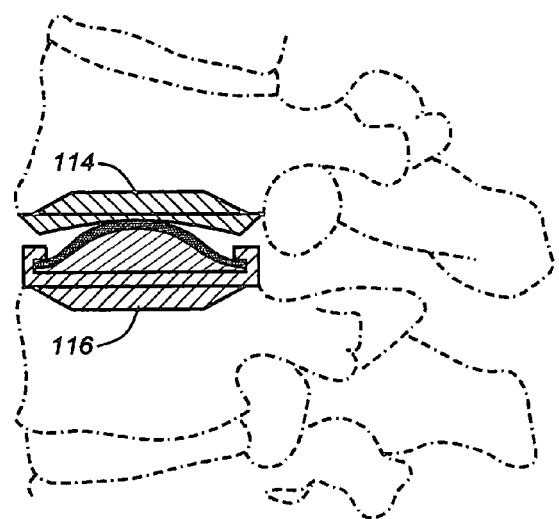
FIG. 20 is a sagittal cross section of the spine and a single cylinder embodiment of the ADR shown in FIG. 7.

FIG. 20 is a sagittal cross section of the spine and a single cylinder embodiment of the ADR drawn in FIG. 7. Keels from the ADR EPs project into the vertebrae above and below the ADR.

Figure 21A:
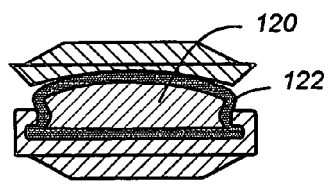
FIG. 21A is a sagittal cross section of an alternative embodiment of the ADR.
Figure 21B:
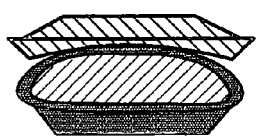
FIG. 21B is a sagittal cross section through another embodiment of the ADR shown in FIG. 21A.

FIG. 21A is a sagittal cross section of an alternative embodiment of the ADR. The cushion element (area of the drawing with widely spaced diagonal lines) is located into a somewhat flexible shell (dotted area of the drawing). The shell completely isolates the cushion element from exposure to the fluids of the body. The walls of the shell reversibly bend in response to axial loads. The shell could be made of plastic, polyethylene, or a flexible metal such as titanium. The upper ADR EP articulates with the shell. The shell may either articulate with lower ADR EP or the shell may snap into the lower ADR EP. The shell could be filled with a liquid form of the cushion material. The cushion material could polymerize, or cure, within the shell. The thickness of the walls of the shell could vary. For example, the top and bottom of the shell could be thicker than the sides of the shell. The thin side walls would encourage bending through the side walls rather than the top and bottom of the shell. FIG. 21B is a sagittal cross section through another embodiment of the ADR drawn in FIG. 21A. The cushion material is contained within a hollow area in the inferior ADR EP. The upper and lower ADR EPs articulate.

Figure 22:
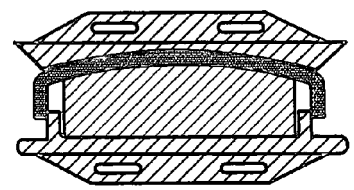
FIG. 22 is a sagittal cross section of an alternative embodiment of the ADR shown in FIG. 5A.

FIG. 22 is a sagittal cross section of an alternative embodiment of the ADR drawn in FIG. 5A. The bottom component of the ADR drawn in FIG. 5A has a keel to attach the ADR to the vertebra inferior to the ADR. The upper component of the ADR drawn in FIG. 5A articulates with an ADR EP. The gap between the walls of the ADR and the cushion element allow the cushion element to expand radially with axial compression. Elastomers that contain air, such as "foam polyurethane" require less space for expansion with axial loads. The air within the elastomer is compressible.

Figure 23A:
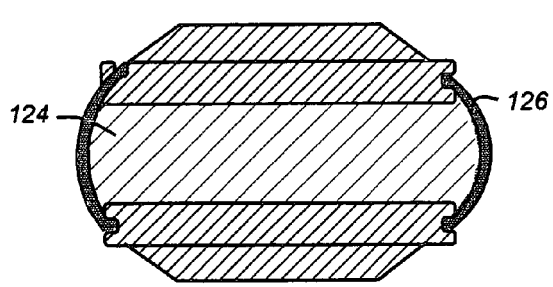
FIG. 23A is a sagittal cross section through yet another embodiment of the ADR of the present invention.
Figure 23B:
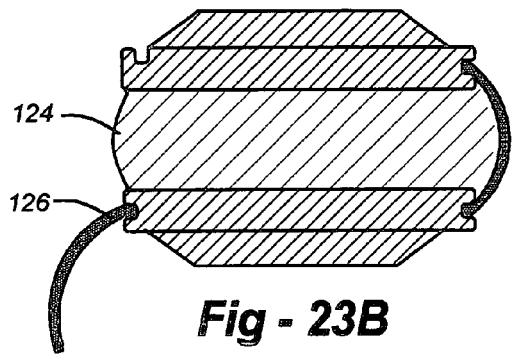
FIG. 23B is a sagittal cross section of the embodiment of the ADR shown in FIG. 23A.

FIG. 23A is a sagittal cross section through another embodiment of the ADR. The cushion element is contained between ADR EPs. A flexible band attaches to the upper and lower ADR EPs. The flexible band could prevent exposure of the cushion element to the fluids of the body. The cushion element is not attached to either ADR EP. Fluid, such as vegetable oil, could be contained within the ADR. Alternatively, the outer, flexible band could be fluid permeable to permit fluid transfer in hydrogel containing embodiments. FIG. 23B is a sagittal cross section of the embodiment of the ADR drawn in FIG. 23A. A portion of the outer band can be detached from one of the ADR EPs to create a window into the ADR. The cushion element can be replaced through the window. The new cushion element could be sealed by a "fluid tight" membrane. The fluid tight membrane could also contain a fluid. The outer band could be reattached to the upper ADR EP after changing the cushion element. Hydrogel containing embodiments would not require a detachable outer band. The hydrogel containing embodiment could be placed into the disc space with a partially dehydrated hydrogel. The outer band would no longer be required to provide a fluid impermeable barrier. Further, in FIG. 23A, the outer, flexible band could be fluid permeable to permit fluid transfer in hydrogel containing embodiments. Note also that in FIG. 23B, the hydrogel containing embodiments would not require a detachable outer band since the device could be placed into the disc space with a partially dehydrated hydrogel.

Figure 23C:
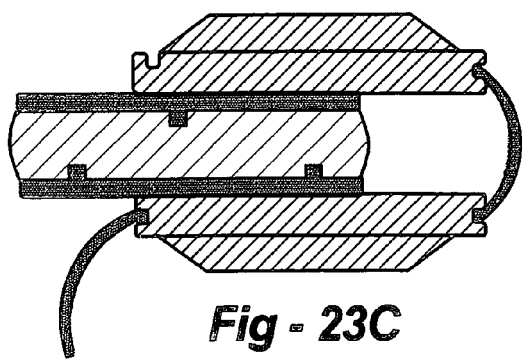
FIG. 23C is a sagittal cross section through an alternative embodiment of the ADR drawn in FIG. 23B.

FIG. 23C is a sagittal cross section through an alternative embodiment of the ADR drawn in FIG. 23B. The cushion element is capped with a material that reduces friction between the ADR EPs and the cushion component. For example, polyethylene or chrome cobalt caps could press fit into the top and bottom of the cushion element.

FIG. 24A is a sagittal cross section through another embodiment of the ADR. The ADR has a novel keel that limits shear stress on the cushion element. The keel allows at least 10 degrees of flexion, 5 degrees of extension, and 2.5 degrees of lateral bending in each direction, and 2 degrees of axial rotation in each direction. A donut shaped cushion element surrounds the keel. FIG. 24B is a coronal cross section through the ADR drawn in FIG. 24A. The keel of the upper ADR EP cooperates with a slot within the lower ADR EP to allow the motions mentioned above.

FIG. 25 is a lateral view of the spine and a multi-component embodiment of the ADR drawn in FIG. 2A. Multiple cushion components are connected together. For example, the components can be connected to a band that surrounds the components. The cushion components could rotate about axles connected to the band. FIG. 26 is a sagittal cross section through the embodiment of the ADR drawn in FIG. 5A. The two components are connected by a flexible tension band. The band prevents dissociation of the components.

By way of a succinct summation, this invention broadly encases, encapsulates, contains, or protects compressible one or more rigid components associated with an articulating bone to contain and protect the compressible/resilient member. The cushion elements in the preferred embodiments include hydrogels, elastomers, and in particular, "foam polyurethane." The container that surrounds the cushion element may perform multiple advantageous functions, including:

G. Holds the cushion in place.
H. Reduces frictional forces on the cushion element.
I. Reduces shear forces on the cushion element.
J. In some embodiments, seals the cushion element from exposure to the fluids of the body. Body fluids may destroy the cushion element.
K. In some embodiments, retains particle debris.
L. Prevents the growth of tissues into the ADR. Tissue ingrowth may limit the motion of ADRs.

In one preferred embodiment, an ADR has been disclosed that incorporates a polymer cushion element, including elastomers and hydrogels, surrounded by a rigid component or rigid components, to accommodate repeated compression of the cushion element by movement of the rigid component or between the rigid components. This system is may be achieved with or without ADR endplates.

According to a different preferred embodiment, an ADR encloses a polymer cushion element, including elastomers and hydrogels, in a single somewhat flexible metal or plastic component. Alternatively, an ADR with a modular cushion element can be replaced through a removable portion of an outer surrounding component. The surrounding component itself can also be removable. Another ADR according to the invention uses thin rigid liners over elastomer to reduce the friction between the elastomer and ADR EPs. A different embodiment incorporates a novel, motion-limiting keel.

Elastomers, or other polymers, may be provided with caps to reduce friction and wear on the polymer. More than two disc spacer ADRs (ADR without endplates) may be interconnected (as shown in FIG. 25); more than one polyurethane component may be present in an ADR, and more than two components may interact to limit axial rotation, as shown in FIG. 7.

We claim:

1. A prosthetic structure, comprising:
   a first rigid component having a peripheral wall with an outer surface;
   a second rigid component having a peripheral wall with an inner surface;
   the components being nested with the inner and outer surfaces in sliding engagement creating an enclosed cavity; and
   a compressible/resilient hydrogel disposed within the cavity.

2. The prosthetic structure according to claim 1, further including one or more channels through at least one of the elements to permit fluid transfer.

* * * * *